US006770302B2

(12) United States Patent
Mitra et al.

(10) Patent No.: US 6,770,302 B2
(45) Date of Patent: Aug. 3, 2004

(54) **INDIAN GREEN MUSSEL (*PERNA VIRIDIS*) AS A SOURCE OF ANTI-HIV ACTIVITY**

(75) Inventors: Debasis Mitra, Pune (IN); Anil Chatterji, Goa (IN)

(73) Assignees: Department of Biotechnology, New Delhi (IN); Council of Scientific and Industrial Research, Rafi Marg (IN)

( * ) Notice: Subject to any disclaimer, the term of this patent is extended or adjusted under 35 U.S.C. 154(b) by 0 days.

(21) Appl. No.: 10/112,081

(22) Filed: Mar. 29, 2002

(65) Prior Publication Data

US 2002/0168416 A1 Nov. 14, 2002

Related U.S. Application Data

(60) Provisional application No. 60/280,086, filed on Mar. 30, 2001.

(51) Int. Cl.[7] ................................................. A61K 35/56
(52) U.S. Cl. ....................................................... 424/547
(58) Field of Search ........................................... 424/547

(56) References Cited

PUBLICATIONS

Gait and Karn (Tibtech (1995), vol. 13, pp. 430–438).*
Flexner and Hendrix (AIDS: Biology, Diagnosis, Treatment, and Prevention, fourth edition, edited by DeVita et al. Lippincott–Raven Publishers, 1997, Chapter 22).*

* cited by examiner

*Primary Examiner*—Leon B. Lankford, Jr.
*Assistant Examiner*—Susan D. Coe
(74) *Attorney, Agent, or Firm*—Ladas & Parry

(57) ABSTRACT

The present invention relates to the use of Indian Green Mussel (*Perna viridis*) as a source of anti-HIV activity. More particularly, the present invention relates to the use of an extract of Indian Green Mussel (*Perna viridis*) as a source of anti-HIV activity in vitro.

10 Claims, 2 Drawing Sheets

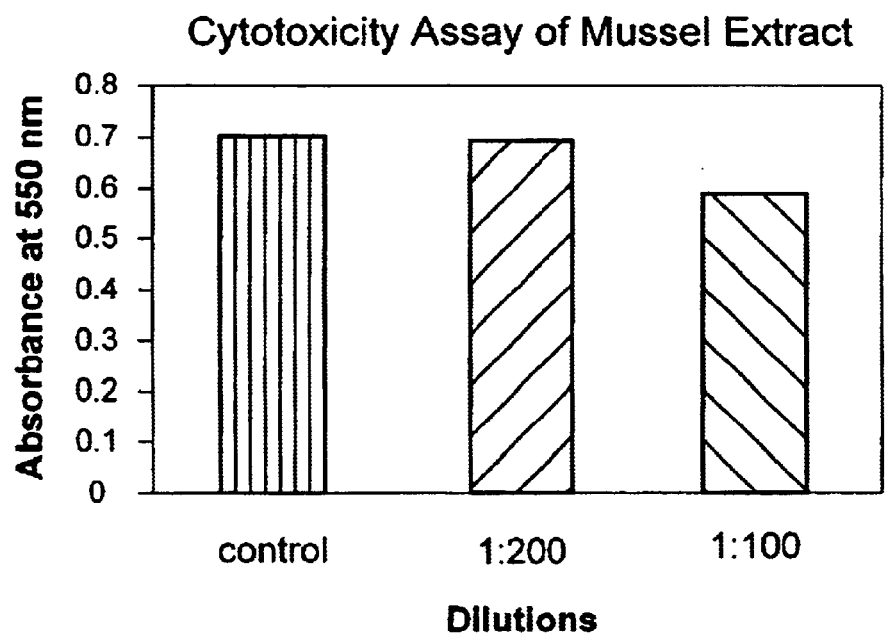
F I G. 1
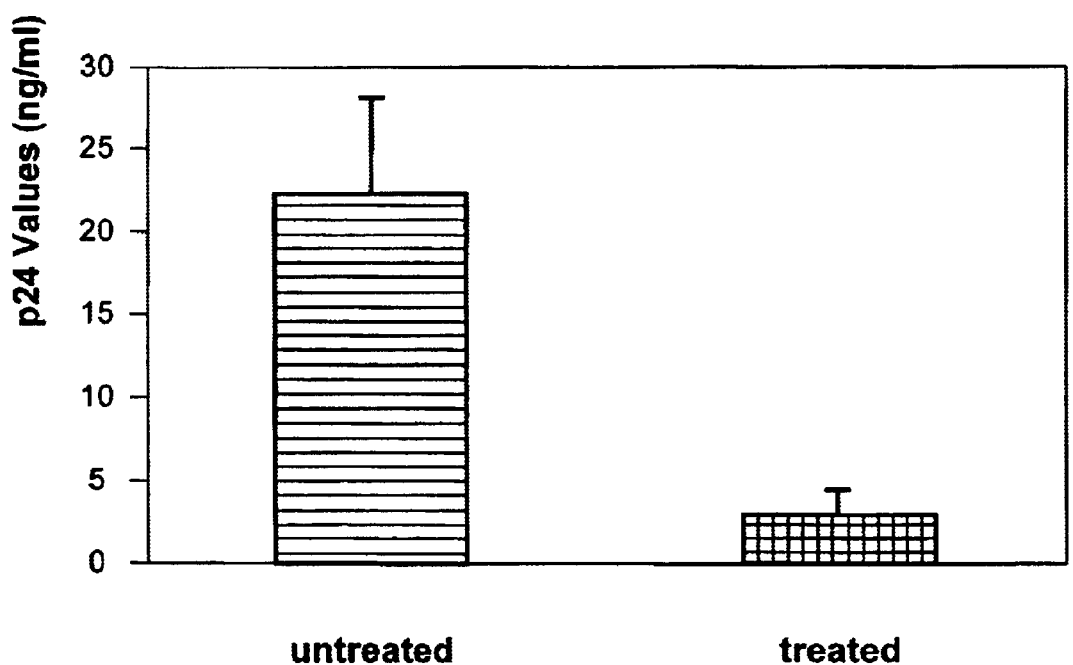
F I G. 2

INDIAN GREEN MUSSEL (PERNA VIRIDIS) AS A SOURCE OF ANTI-HIV ACTIVITY

This application claims the benefit of provisional No. 60/280,086 filed on Mar. 30, 2001.

FIELD OF THE INVENTION

The present invention relates to the use of Indian Green Mussel (*Perna viridis*) as a source of anti-HIV activity. More particularly, the present invention relates to the use of an extract of Indian Green Mussel (*Perna viridis*) as a source of anti-HIV activity in vitro.

BACKGROUND OF THE INVENTION

The incidence of HIV infection, the cause of acquired immunodeficiency syndrome (AIDS) has reached catastrophic levels worldwide including India. For example, it is reported that India already has the largest burden of HIV infection in the world. Extensive work is being done throughout the globe to identify new anti-HIV therapeutic strategies to fight the killer virus. One strategy has been to identify anti-HIV compounds in natural resources like marine flora and fauna.

Antiviral activity of extracts from a variety of marine plants and animals have been studied and some results have been very encouraging. There are more than 100,000 species of molluscs, an antiviral and antibacterial substances have been extracted from clams, oysters, sea snails, etc. The marine mussels are another group of bivalve molluscs, which have compounds of high biomedical properties. The mussels are not only a cheap source of protein for human consumption but also found to possess some complex bio-active compounds which have tremendous potential in medical science. Brown mussel hydrolysate is available for human use in Russian market with trade names Viramid and Midel as antiviral drugs.

Carrageenan, a cell wall polysachharide from red algae, has been shown to be effective against *Herpes simplex* virus, a major co-infection in AIDS patients (Richards, J. T. et al., 1978, *Antimicrobial. Agents Chemother.*, 14, 24–30). Tunicate extracts have shown promising results as antivirals. Organic antivirus has been isolated from Didemmun sp. (Rinehart, K. L., et al., 1981, *Science* 212, 933–935), specifically an HIV-1 protease inhibitor termed Didemnaketal A (Potts, H. C. M., et al, (1991), *J. Am. Chem. Soc, b 113, 6321* pp).

Mercenene, an extract from the clam, Mercenaria sp has been shown to have antiviral properties (Li, C. P. et. al., (1974), *Cancer Chemother. Rep.* Part 24, 97–129).

The extract from Indian green mussel (*Perna viridis*) has earlier been found to be active against influenza, herpes and hepatitis viral strains. The process of preparation of extract was first developed by the Russian scientists (Patent No. RU 2043109). A process on extraction of mussel hydrolysate is also disclosed in Indian patent application No 493/DHL/99.

While several drugs are available commercially for the inhibition of HIV-1 virus, the cost of such drugs is prohibitive.

OBJECT OF THE INVENTION

The main object of the present invention is to identify anti-HIV activity in the extract prepared from the Indian green mussel *Perna viridis*.

It is another object of the invention to identify a natural source for biomolecules useful as anti-HIV agents.

It is another object of the invention to identify and isolate anti-HIV biomolecules from marine organisms.

It is a further object of the invention to identify and characterize anti-HIV activity in the Indian marine bivalve, *Perna viridis*.

It is another objective of the invention to identify a bio-active molecule with anti-HIV activity in Indian green mussel for therapeutic intervention in AIDS.

SUMMARY OF THE INVENTION

Accordingly, the present invention relates to the use of extract of Indian green mussel (*Perna viridis*) as a source of anti-HIV activity in vitro.

In one embodiment of the invention, the extract comprises the mussel hydrolysate.

In another embodiment of the invention, the mussel hydrolysate is used in 1,200 dilution.

The present invention also relates to the use of extract of Indian green mussel (*Perna viridis*) for anti-HIV activity in vitro, which comprises preparing an extract from the Indian green mussel (*Perna viridis*), establishing non-toxicity at the dilution (1:200) on human T-lymphocytic cell line CEM using MTT assay, assessment of production of virus in supernatants of the treated and untreated infected cells by p24 antigen ELISA using HIV-1 NJ4.3 isolate in T-cell lines CEM and Jurkat and using HIV-1 IIIB isolate in monocytic cell line U937.

In one embodiment of the invention, the extract is found to be non-toxic at the dilution (1:200) on human T-lymphocytic cell line CEM using MTT assay.

In another embodiment of the invention, the supernatants of the treated and untreated infected cells is subjected to p24 antigen ELISA to assess the production of virus using HIV-1 NL4.3 isolate in T-cell lines CEM and Jurkat and using HIV-1 IIIB isolate in monocytic cell line U4937.

BRIEF DESCRIPTION OF THE DRAWINGS

FIG. 1 is a graph showing the results of an MIT assay for the cytotoxicity of the green mussel hydrolysate on human CD4+T cell line CEM cells. The assay was performed by incubating $10^4$ cells in 100 $\mu l$ medium for 72 hours followed by addition of MTT;

FIG. 2 is a graph showing the effect of green mussel hydrolysate on HIV-1 NL 4.3 infected GEM cells. Infected cells were treated with hydrolysate (1:200 dilution) and the supernatant was tested for virus production by p24 antigen ELISA;

DETAILED DESCRIPTION OF THE INVENTION

Figure 3:
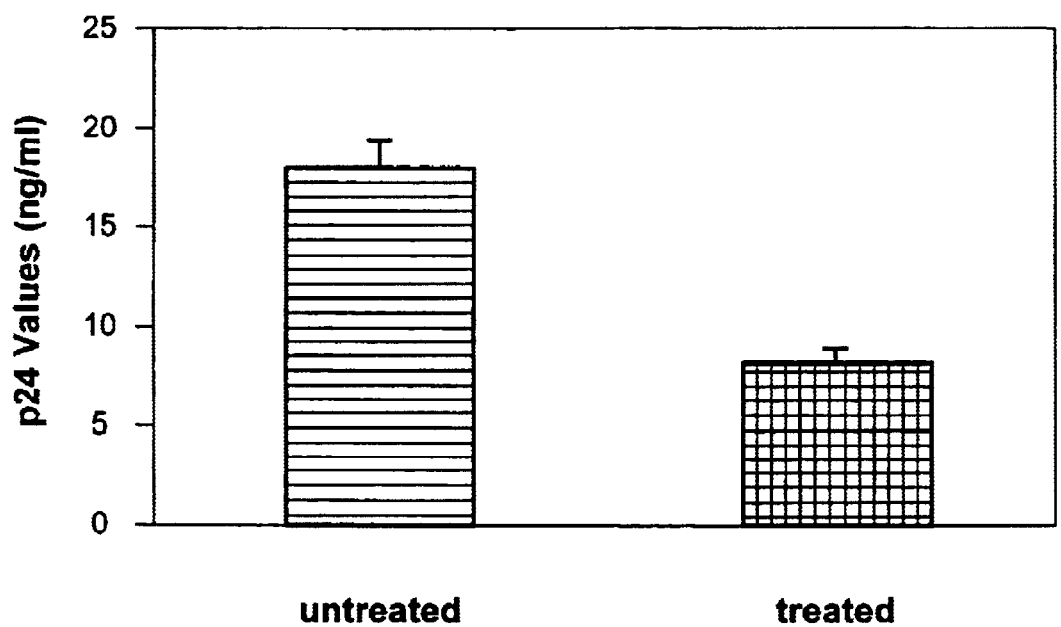
FIG. 3 is a graph showing the effect of green mussel hydrolysate on HIV-1 NL 4.3 infected Jurkat cells. Infected cells were treated with hydrolysate (1:200 dilution) and p24 values of the supernatant were measured.

The extract prepared from the Indian marine bivalve, *Perna viridis* was tested for anti HIV activity by initially testing the extracts for cytotoxicity on human T-lymphocytic and monocytic cell lines such as CEM, Jurkat, U937, using standard cell viability assay. The effect of the extract from the mussel *Perna viridis* on HIV was tested by a number of assays. The initial screening was done using the HIV-1 cytotoxicity assay. The measurement of cell viability of HIV infected cells in presence and absence of the extract was carried out boy XTT-Formazan assay. The supernatants of the treated and untreated infected cells was subjected to p24 antigen ELISA to assess the production of virus in presence of the extract. All the experiments was initially done using laboratory isolates and then was followed by primary isolates of different sub-types including sub-types prevalent in India.

Results

In the preliminary experiment the Indian green mussel extract was incubated with human monocytic cell line U937 infected with HIV-1 for 48 hours. The HIV-1 p24 antigen assay of the culture supernatants resulted in almost 40–50% inhibition of virus production in treated cells as compared to the controls showing that the extract prepared from marine bivalve, *Perna viridis* has potential to develop into an anti-HIV drug.

The extracts of the marine bivalve, *Perna viridis*, show and anti-HIV activity. The extracts when incubated with human monocytic cell line infected with HIV-1 show 40 to 50% inhibition of virus production in treated cells as compared to the controls.

Indian green mussed was chosen as the marine bivalve in view of its abundance off the coastline of India rendering the process for the extraction economical.

Preparation of Extract from Marine Bivalves

Live green mussels collected from the natural environment were deshelled and meat and mantle fluid was removed. The mixture of mantle fluid and meat was fermented at 40° C. for two hours. Distillation and digestion process was carried out with concentrated hydrochloric acid at 100+5° C. for 20 hours. The resultant solution was neutralized with an alkali at room temperature to achieve a pH of 5.6. The active extract was isolated by keeping the solution in a separating flask and carefully removing the middle part of the solution after allowing the extract for settlement for 15 days. Process of preparation of extract from the marine bivalves is disclosed in the applicants copending application (CSIR Reference: NF 159/00).

Screening for Anti-HIV Activity

The extract prepared the Indian green mussel was tested for cytotoxicity on human T-lymphocytic cell line CEM using MTT assay. Human T-lymphocytic cell lines like CEM, Jurkat and monocytic cell line U937 were infected with HIV-1 isolate NL4.3 and HIV-1 IIIB respectively were incubated in the presence acquired absence of the mussel hydrolysate. The supernatants of the treated and untreated infected cells were subjected to p24 antigen. ELISA to assess the production of virus.

In a preliminary experiment in our laboratory the Indian green mussel extract was incubated with human monocytic cell lines U937 infected with HIV-1 of 48 hours. The HIV-1 p24 antigen assay of the culture supernatants revealed that there was almost 10–50% inhibition of virus production in treated cells as compared to the controls. This showed that extract prepared from marine bivalve, *Perna viridis* has a great potential to develop an anti-HIV drug.

The novelty and inventive steps of the present invention is in the identification of anti-IIIV activity in vitro in the extract of green mussel for therapeutic intervention of AIDS.

EXAMPLE 1

The mussel hydrolysate was tested for cytotoxicity using human T-lymphocytic cell line CEM at various dilutions. The assay was performed using $10^4$ cell in 0.1 ml of media (RPMI with 10% PCS) for 72 hours. The extract was found to be non-toxic at the dilution of 1:200 using MTT assay (FIG. 1).

EXAMPLE 2

CEM cells were infected with HIV-1 NL4.3 isolate and were incubated with the mussel hydrolysate (1:200 dilution). The supernatants of the treated and untreated infected cells were subjected to p24 antigen ELISA to assess the production of virus after 9 days of infection and incubation with the mussel hydrolysate. The results showed about 85% inhibition of HIV-1 virus production in presence of mussel hydrolysate (FIG. 2).

EXAMPLE 3

Jurkat cells were infected with HIV-1 NL4.3 isolate and were incubated with the mussel hydrolysate (1:200 dilution). The supernatants of the treated and untreated infected cells were subjected to p24 antigen ELISA to assess the production of virus after 9 days of infection and incubation with the mussel hydrolysate. The results showed more than 50% inhibition on or HIV-1 virus production in presence of mussel hydrolysate (FIG. 3).

EXAMPLE 4

Figure 4:
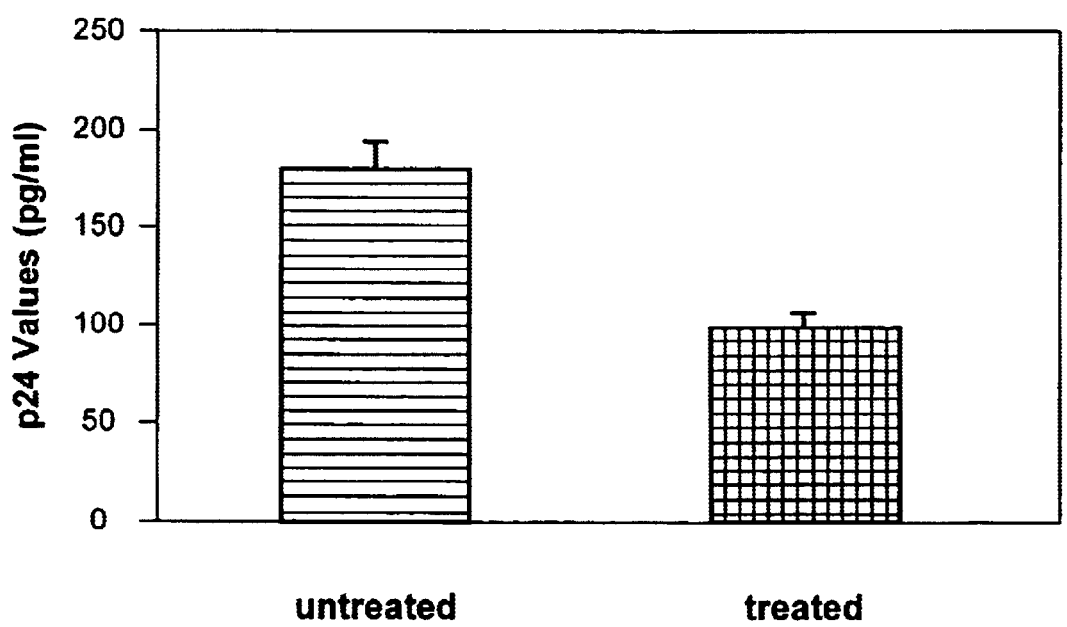
FIG. 4 is a graph showing the effect of green mussel hydrolysate on HIV-1 IIIB infected U937 cells. Infected cells were treated with hydrolysate (1:200 dilution) and p24 values of the supernatant were measured.

Monocytic cell line U937 was infected with IIIV-1 IIIB isolate and was incubated with the mussel hydrolysate (1:200 dilution). The supernatants of the treated and untreated infected cells were subjected p24 antigen ELISA to assess the production of virus after 11 days of infection and incubation with the mussel hydrolysate. The results showed about 50% inhibition of HIV-1 virus production in presence of mussel hydrolysate (FIG. 4).

Advantages

Identification of anti-HIV activity in the Indian green mussel *Perna viridis* and its use in management of HIV disease, AIDS. Since marine bivalve are a natural source and available in abundance along the Indian coastline, development of anti-HIV drug will be economically viable.

REFERENCES

1. Li, C. P., Goldin, A., and Hartwell, J. L. (1974) Antineoplastic substances from the sea; a review *cancer chemotherapy*; Ref-2 4(3) 97–129.
2. Polts, D. C., 1991, *J. Am. Chem. Soc*, 113, 6321 pp.
3. Richard J. T., Kern E. R., Glaspow, L. A., Overall, J. C., Deyn E. F., and Hatch, M. T. (1978). Antiviral activity of extract from marine Algae. *Antimicrobial. Agents Chemotherapy*, 14, 24–30.
4. Rinehart, K. L., Gloer, J. B., Hugues, R. G., Rehis, H. H., McGoverny J. P., Swynaberg, E. B., Stringfellow, D. A., Kwntzel, S. L. and Li, L. H. (1981). Didemnins; antiviral and antitumor depsipeptides from a caribbean tunicate *Science*, 212, 933–935.

We claim:

1. A method for inhibiting HIV virus in a cell line comprising contacting the cell line with an Indian green mussel extract.

2. The method according to claim 1, wherein the extract is a mussel hydrolysate.

3. The method according to claim 2, wherein the hydrolysate comprises a diluted mixture of meat and mantle fluid extracted from Indian green mussels.

4. The method according to claim 3, wherein the hydrolysate comprises a 1:200 dilution of the mixture.

5. The method according to claim 1, wherein the cell line is selected from the group consisting of human T-lymphocytic cell line CEM, Jurkat cells and monocytic cell line U937.

6. The method according to claim 1, wherein the HIV virus is selected from the group consisting of HIV-1 IIIB and HIV-1 NL 4.3.

7. The method according to claim 1, comprising testing the extract for non-toxicity prior to said contacting.

8. The method according to claim 7, wherein said testing is performed on a human T-lymphocytic cell line CEM with an MTT assay.

9. The method according to claim 8, wherein said testing is performed using a 1:200 dilution of a mixture of meat and mantle fluid removed from Indian green mussels.

10. The method according to claim 1, wherein said contacting is performed in vitro.

* * * * *